United States Patent [19]

Elsner et al.

[11] 4,324,919

[45] Apr. 13, 1982

[54] PRODUCTION OF TERTIARY PHOSPHINES

[75] Inventors: Georg Elsner, Hürth; Hartfrid Vollmer, Erftstadt; Ernst Reutel, Bonn, all of Fed. Rep. of Germany

[73] Assignee: Hoechst Aktiengesellschaft, Fed. Rep. of Germany

[21] Appl. No.: 183,057

[22] Filed: Sep. 2, 1980

[30] Foreign Application Priority Data

Sep. 7, 1979 [DE] Fed. Rep. of Germany ....... 2936210

[51] Int. Cl.$^3$ .............................................. C07F 9/50
[52] U.S. Cl. ...................................................... 568/8
[58] Field of Search ............................................ 568/8

[56] References Cited

U.S. PATENT DOCUMENTS 2,584,112 2/1952 Brown .................................... 568/8
2,803,597 8/1957 Stiles ...................................... 568/8
2,822,376 2/1958 Hechenbleikner et al. ............ 568/8

Primary Examiner—Helen M. S. Sneed
Attorney, Agent, or Firm—Connolly and Hutz

[57] ABSTRACT

The invention relates to a process for making tertiary phosphines of the general formula $R_3P$, in which R stands for a linear alkyl radical having 2 to 4 carbon atoms. To this end, hydrogen phosphide is reacted with linear monoolefins having 2 to 4 carbon atoms. More particularly, the tertiary phosphine which is desired to be made is dissolved in an inert solvent and $PH_3$ and monoolefin are reacted in the solution.

1 Claim, No Drawings

PRODUCTION OF TERTIARY PHOSPHINES

The present invention relates to a process for making tertiary phosphines of the general formula $R_3P$, in which R stands for a linear alkyl radical having 2 to 4 carbon atoms, wherein hydrogen phosphide is reacted with a linear monoolefin with 2 to 4 carbon atoms, the reaction being normally carried out under pressure and at elevated temperature in the presence of an agent yielding free radicals.

A process for reacting hydrogen phosphide with an aliphatic monoolefin in a desirable quantitative ratio at elevated temperature has been described, e.g. in German Pat. No. 899 040. This is a process wherein equivalent proportions of hydrogen phosphide and butene-(1), respectively, are reacted in the presence of a peroxide as a radical-yielding agent, to give tributylphosphine which is obtained in a yield of about 33% after a 16 hour reaction period.

By subjecting a mixture of hydrogen phosphide and isobutene in a glass vessel to irradiation with ultraviolet light at 20° C., it is also possible by the process just described to produce triisobutylphosphine, which is obtained in a yield of about 13.5%, after 150 minutes.

Adverse effects which are associated with this prior process reside in the fact that the final product is obtained in commercially unsatisfactory yields, or in the formation of substance mixtures which are difficult to separate into their components.

It has also been described (cf. G. M. Burch et al., Journal of the Chemical Society, pages 1083 et seq.) that hydrogen phosphide and ethylene can be reacted in a molar ratio of 1:1 with irradiation of ultraviolet light. In this process, triethylphosphine is obtained in good yields (67%, based on olefin) but the space/time yield of $8.9 \cdot 10^{-5}$ mol/l·h does not contribute to commercial attractiveness of this prior process.

A still further process has been described (cf. M. M. Rauhut et al., Journal of Organic Chemistry, 1961, 26, page 5138 et seq) wherein isobutylene, for example, is reacted with $PH_3$ under elevated pressure and in a solvent, if desired, under the action of an agent yielding free radicals. Reaction to tertiary phosphines occurs to some slight extent only, and use is made exclusively of cyclic, long chain or branched olefins.

It is therefore an object of the present invention to avoid the adverse effects described hereinabove and to provide a process for making short chain tertiary phosphines which permits these compounds to be obtained in commercially attractive space/time-yields and can be carried out under reasonably low pressure without expensive machinery.

To this end, the invention unexpectedly provides for a tertiary phosphine which is desired to be made to be dissolved in an inert solvent and for the $PH_3$ and monoolefin to be reacted in the solution.

A preferred feature provides for the tertiary phosphine to be used in the solution in a proportion of 50 to 500 mol%, based on $PH_3$.

A further preferred feature provides for the reaction to be effected at temperatures of 50° to 200° C. and under pressures initially of 5 to 25 bars.

The present process has the following technically beneficial effects. It avoids the need to use high pressure. By increasing the working temperature, it is possible to accelerate the decomposition of the radical-yielding initiator and in this way considerably to shorten the reaction period. It is more especially possible by dropwise addition of the radical-yielding initiator to control the exothermal reaction and avoid excessively high temperature and pressure inside the reactor.

The following Examples illustrate the invention.

EXAMPLE 1: (Comparative Example)

$PH_3$ and ethylene were introduced under slight overpressure into an 80 l-autoclave. The two components were used in a quantity necessary to avoid formation of a pressure higher than 25 bars at 120° C., on the basis of van der Waals constant. This corresponded to the use of 15.5 mols (0.527 kg) $PH_3$ and 46.5 mols (1.302 kg) ethylene.

Next, the autoclave was heated from the outside to about 90° C. and initiator solution (1 l/h saturated solution of azo-bis-isobutyronitrile in toluene) was introduced in metered proportions. The exothermal reaction made the temperature increase to about 110° C. and the pressure, which had initially increased to 22 bars, decreased gradually. After about 2 hours, the exothermal reaction was found to subside, and it was necessary for the reaction temperature of about 90° to 110° C. to be maintained by heating from the outside. After the initiator solution had been added over a period of about 5 hours, the pressure prevailing inside the reactor had dropped to about 3 bars. A specimen was subjected to gas-chromatographical analysis. An about 27 weight % solution of triethylphosphine in toluene with merely slight proportions of monoethylphosphine and diethylphosphine was found to have been formed. The yield, based on $PH_3$, was 90 weight %; this corresponded to a space/time-yield of $3.5 \cdot 10^{-2}$ mol/l·h.

EXAMPLES 2 to 5: (Invention)

The procedure described in Example 1 was repeated 4 times; the reaction product obtained in each case was allowed to remain in the autoclave and used as starting batch in the next following reaction. The pressure inside the reactor was found to decrease from batch to batch although the free volume which remained inside the reactor became increasingly smaller. At the same time, it was possible to reduce to about 50% the necessary quantity of initiator solution without the conversion rate being reduced. Altogether 26.5 l of an about 39 weight % solution of triethylphosphine in toluene was obtained; this corresponded to a yield of 95 weight %, based on $PH_3$.

EXAMPLE 6

The 39% triethylphosphine solution in toluene made as described in Examples 2 to 5 was cooled down to about −20° C., inside the autoclave. Introduced thereinto under slight overpressure were 1.55 kg $PH_3$ and 3.9 kg ethylene and the whole was then heated to about 90° C. The pressure increased to about 20 bars. The reaction was started by the introduction by means of a pump of a small proportion of the initiator solution of Example 1. The temperature increased rapidly to about 120° C., and the pressure decreased rapidly. Altogether 2 l of initiator solution was introduced within 2 hours. Towards the end of the reaction, the pressure dropped down to 2 bars. Gas-chromatographic analysis indicated that the product was an about 47 weight % solution of triethylphosphine. This corresponded to a yield of 95 weight % and to a space/time-yield of $2.9 \cdot 10^{-1}$ mol/l·h.

EXAMPLE 7

As described in Examples 2 to 5, an about 50% solution of tri-n-propylphosphine in toluene was prepared by repeated reaction in each particular case of 0.52 kg $PH_3$ with 2 kg propene in the presence of a free radical-yielding agent, and the solution so obtained was used as starting material. Next, 1.5 kg hydrogen phosphide and 6 kg propene were reacted therein, as described in Example 6. On heating the material to reaction temperature of 90° C., the pressure rose to only about 20 bars. The reaction was effected in the manner described in Example 6. After about 2 hours, the pressure was found to have dropped to 2 bars. The reaction solution was analyzed. It was an about 58 weight % solution of tri-n-propylphosphine in toluene. This corresponded to a yield of 93 weight % and to a space/time-yield of $2.9 \cdot 10^{-1}$ mol/l·h.

EXAMPLE 8

0.52 kg $PH_3$ and 2.6 kg butene-(1) were reacted as described in Example 7 to give an about 50% solution of tri-n-butyl-phosphine in toluene. Introduced thereinto under slight overpressure were 16.2 kg butene-(1) and 2.82 kg $PH_3$. The whole was heated to about 70° C. and initiator solution was metered thereinto. The exothermal reaction made the temperature increase to 106° C. and the pressure to 23 bars. Altogether 3 l initiator solution was added within 3 hours. The pressure was then found to have dropped to 5 bars (at 120° C.). The whole was allowed to cool, a specimen was taken and analyzed gas-chromatographically. It was an about 67% tributylphosphine solution in toluene, corresponding to a conversion rate of more than 95%, based on butene and $PH_3$.

As can be seen from the present Example, the process of this invention compares very favorably with the prior art methods. The space/time-yield was $7.25 \cdot 10^{-1}$ mol/l·h.

We claim:

1. In the process for making tertiary phosphines of the general formula $R_3P$, in which R stands for a linear alkyl radical having 2 to 4 carbon atoms, by reacting hydrogen phosphide with linear monoolefins having 2 to 4 carbon atoms under pressures of 5 to 25 bars and temperatures of 50° to 200° C. in the presence of an agent yielding free radicals, the improvement which comprises: preparing a solution of the tertiary phosphine which is desired to be made, in an inert solvent, and performing the reaction of the $PH_3$ with the monoolefin in said solution, which is used in such amounts that the tertiary phosphine in the solution is applied in a proportion of 50 to 500 mol%, based on $PH_3$.

* * * * *